United States Patent
Schatz et al.

(10) Patent No.: US 6,916,176 B2
(45) Date of Patent: Jul. 12, 2005

(54) ROTATION LOCK DEVICE FOR PREVENTING UNDESIRED ROTATION OF A SHAFT ESPECIALLY FOR HANDPIECES USED IN MEDICAL TREATMENTS

(75) Inventors: Norbert Schatz, Buermoos (AT); Thomas Jindra, Buermoos (AT)

(73) Assignee: W&H Dentalwerk Burmoos GmbH (AT)

(*) Notice: Subject to any disclaimer, the term of this patent is extended or adjusted under 35 U.S.C. 154(b) by 90 days.

(21) Appl. No.: 10/654,187

(22) Filed: Sep. 2, 2003

(65) Prior Publication Data

US 2004/0063065 A1 Apr. 1, 2004

(30) Foreign Application Priority Data

Sep. 26, 2002 (AT) ............................... A 1442/2002

(51) Int. Cl.[7] ............... A61C 1/08; F16D 1/00
(52) U.S. Cl. ................... 433/126; 403/320
(58) Field of Search ................ 433/126, 127, 433/114, 128; 606/80; 279/125; 403/320, 315, 11

(56) References Cited

U.S. PATENT DOCUMENTS

| | | | |
|---|---|---|---|
| 3,827,149 A | * | 8/1974 | Brennan ............... 433/106 |
| 5,490,683 A | * | 2/1996 | Mickel et al. .......... 279/75 |
| 5,498,159 A | * | 3/1996 | Coss .................... 433/126 |
| 6,062,575 A | * | 5/2000 | Mickel et al. .......... 279/75 |

FOREIGN PATENT DOCUMENTS

| DE | 689 10551 T2 | 3/1989 |
|---|---|---|
| WO | WO 99/12491 | 3/1999 |

* cited by examiner

*Primary Examiner*—Cary E. O'Connor
(74) *Attorney, Agent, or Firm*—Klarquist Sparkman, LLP

(57) ABSTRACT

A rotation locking device located in the area of two separate, independent shafts or shaft sections for preventing the undesired rotation of a shaft or shaft section. The rotation locking device includes a locking pin which, in its idle position (during operation of the appliance), rests on a displacement surface of a shaft or shaft section. In the event of the undesired rotation of a shaft (caused, for example, when a tool is being unscrewed from a coupling which is connected to the shafts), the shaft underneath the locking pin turns until the pin is forced out of the displacement surface, is displaced outwards radially and pressed against a component which is fixed to the body of the appliance (e.g. the bearing sleeve of the gearbox in which the rotation locking device is fitted). Any further rotation of the shafts is prevented in this manner.

8 Claims, 3 Drawing Sheets

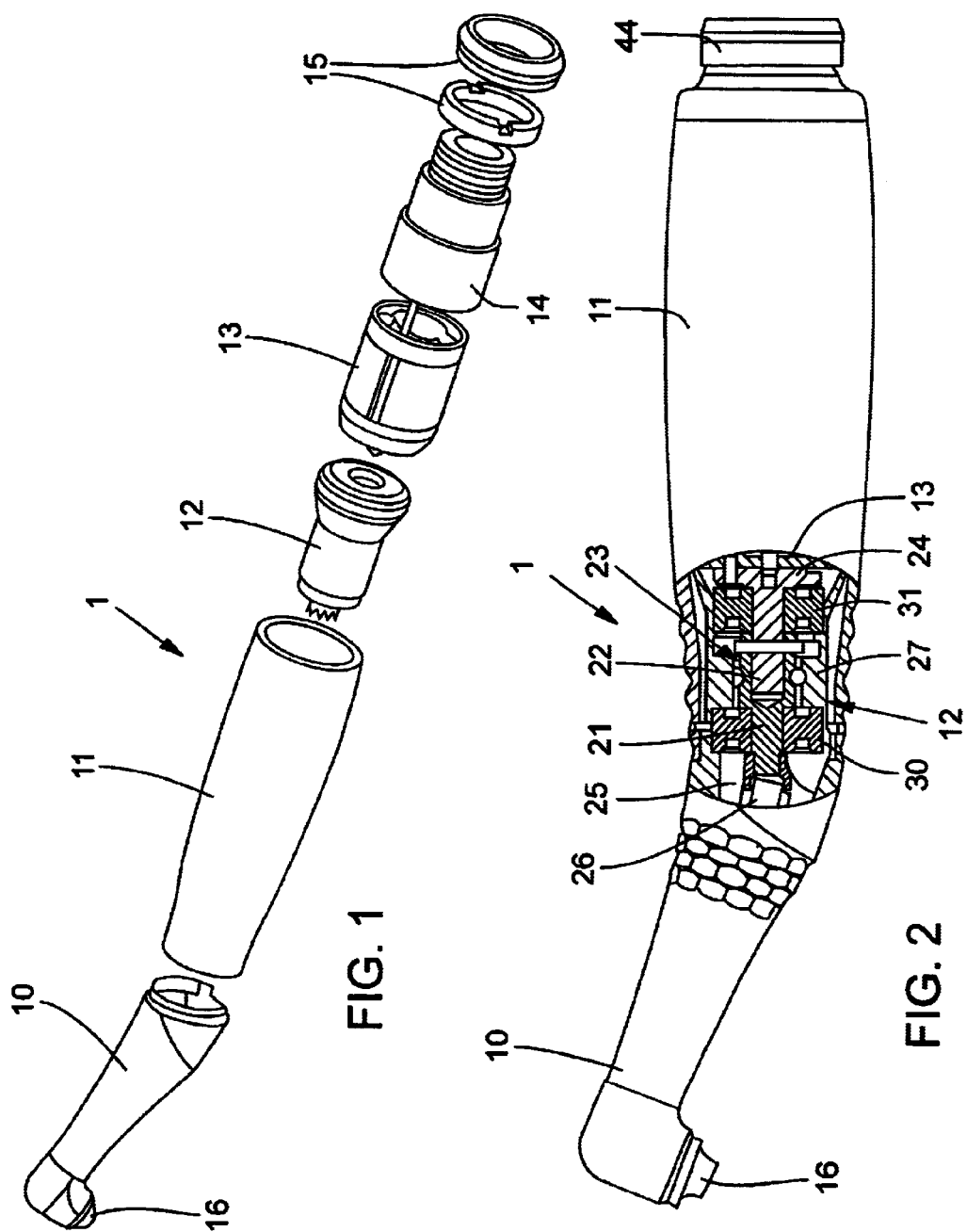

ROTATION LOCK DEVICE FOR PREVENTING UNDESIRED ROTATION OF A SHAFT ESPECIALLY FOR HANDPIECES USED IN MEDICAL TREATMENTS

CROSS REFERENCE TO RELATED APPLICATION

The present application claims priority from pending Austrian Patent Application No. A1442/2002, filed Sep. 26, 2002, which is incorporated herein by reference.

BACKGROUND OF THE INVENTION

1. Field

The invention presented here concerns a rotation lock device located in the area of two separate, independent shafts or shaft sections which is designed to prevent undesired rotation of a shaft or part of a shaft. Rotation lock devices of this type can be used in various appliances in which a tool is driven via shafts. As an example of one possible area of use, which is in no way to be interpreted as a restriction on the total possible fields of use, the rotation lock device is presented below in a contra-angle for prophylactic dental treatment.

2. Description of Prior Art

The aim of preventative dentistry, so-called prophylactic dental treatment, is the prevention of diseases associated with the teeth, mouth and gums. Apart from prophylactic treatment carried out by the individual (cleaning one's teeth at home, for example) the dentist can also perform prophylactic treatment, e.g. removing tartar, plaque and discoloration, or teeth polishing. The latter is mainly carried out using special instruments, e.g. contra-angle and specific tools, such as caps, so-called 'prophy-cups' or brushes. These are secured in the head of the contra-angle by means of a tool coupling and driven by one or more shafts which are connected to a motor.

The tools used are equipped with a threaded pin end which is used to attach the tool to the head of the contra-angle. This pin is screwed into the upper drive (the coupling shaft), which is equipped with the corresponding thread. The upper drive is connected to the motor via at least one other shaft, so that the prophy-cup rotates when the motor runs.

In order to guarantee safe operation the prophy cup must be securely connected to the contra-angle on the one hand, and it should be possible to replace the cup quickly and easily on the other hand. This is necessary for hygienic reasons, as the cup should be replaced (at least) between treatments of different patients. However, sometimes replacement is also carried out during treatment of the same patient.

Tool removal, however, turns out to be extremely difficult in the case of those handpieces or contra-angles presently available on the market: The tool is fitted into the coupling by screwing it in the opposite direction to motor-driven shaft rotation. This is necessary in order to prevent the tool from becoming loose and unscrewing itself out of the coupling during operation, as the pressure on the treatment surface during application and the resulting friction forces act as a brake on the prophy-cup and this then tends to rotate more slowly than the coupling shaft.

On the other hand, however, screwing the tool into the coupling in the opposite direction to shaft rotation means that the tool is often screwed still more tightly into the coupling during treatment, and in order to remove the tool it has to be turned in the same direction as the shaft rotates during operation. The force required to unscrew the tool, which is extremely firmly seated in the head at the end of treatment, is thus often greater than the force required to move the drive shafts. For this reason, when attempting to unscrew the tool from the coupling by hand, the user very often only succeeds in rotating the shafts without loosening the tool.

Treatment paste, which sticks to the tool after the treatment and makes it slippery, makes it even more difficult for the user to remove the tool.

In disclosure document WO 99/12491 A1, a device is described which prevents the drive shaft rotating when the tool is being removed. A pin, which protrudes radially from the front shaft section, is fed into a sliding bearing assembly which is fitted with a helical bore and mounted around the rear drive shaft section. When an attempt is made to remove the tool and this causes the front shaft section to rotate, the pin is turned until it is positioned at the highest point of the helical bore. This causes axial displacement in both shaft sections or shaft extension, which presses against the two bearings. The resistance thus created is sufficient to prevent rotation of the shaft and this makes it possible to unscrew the tool from the coupling.

One disadvantage of this device is that the axial displacement of the shaft sections subjects the bearings to a high loading. In the case of ball bearings, the rollers in the bearing race are compressed, which causes a deterioration in running characteristics. Repeated loading may finally lead to the collapse of the bearings and to related servicing and replacement work, which is expensive both in terms of time and money.

For this reason the invention presented here is based on the task of creating an improved device for preventing the undesired rotation of the shafts when, for example, a tool is being unscrewed from the coupling.

SUMMARY OF THE INVENTION

This task is solved by means of a rotation lock device with the characteristics outlined herein. In accordance with one aspect of the invention, the rotation lock device has a locking pin which, when the tool is unscrewed, is radially displaced (in relation to the axes of the shafts) by the undesired rotation of the shafts caused by the turning action, thus preventing any further undesired rotation of the shafts. In its idle position (during operation of the contra-angle) the locking pin rests on a flattened section of the shaft. While the tool is being removed, the shaft underneath the locking pin turns until the pin is forced out of the flattened section, i.e. is displaced outwards radially and is pressed against a component fixed to the body of the appliance (e.g. the gearbox bearing sleeve, in which the rotation locking device is fitted). Any further rotation of the shaft is prevented by this resistance and the tool can be unscrewed from the coupling. The tool can be unscrewed from the coupling by means of this rotation lock device without the need for any axial displacement of the drive shaft, which subjects the bearings to a heavy loading.

The invention is explained below with the aid of a preferred embodiment and in reference to the enclosed drawings.

BRIEF DESCRIPTION OF THE DRAWINGS

FIG. 1 shows the construction of a contra-angle used in prophylactic treatment in a perspective view.

FIG. 2 shows the contra-angle with an axial sectional view of the gearbox and the rotation locking device.

DETAILED DESCRIPTION OF THE PREFERRED EMBODIMENTS

Figure 3:
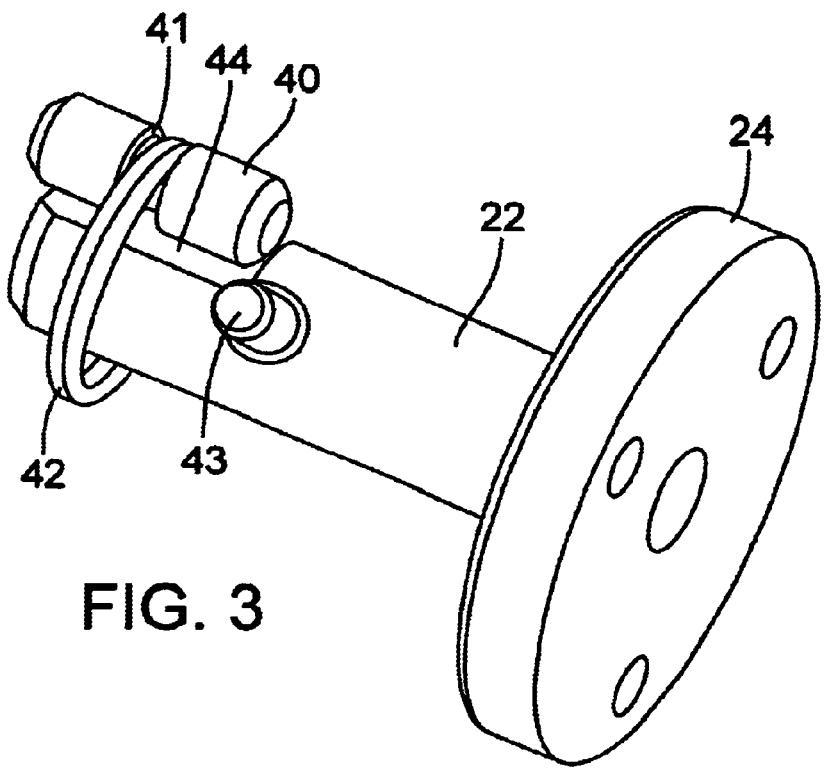
FIG. 3 shows the rear section of the drive shaft of the rotation locking device.

The same components are assigned the same numbers in all diagrams.

The contra-angle, also referred to herein as an appliance, 1 used in prophylactic treatment and shown in FIG. 1 consists of a head unit 10 together with a tool coupling 16, a handle sleeve, or body 11, a gearbox 12, which contains the rotation locking device and a motor driven by compressed air 13. The compressed-air motor 13 is charged with compressed air via a coupling 14 with unions 15 for connection to an intermediate connecting piece or a supply hose. The gearbox 12, the handle sleeve 11 and the head unit 10 contain several shafts (not shown) which transfer the rotational movement of the motor to the tool, e.g. a prophy cup (not shown), which is screwed into the tool coupling 16 before starting the application. Other types of motor can also be used to drive the tool instead of the compressed-air motor 13. The appropriate power supply (e.g. electricity, compressed air, compressed gas etc.) is fed in accordingly via the supply hose to the type of motor used. Since specialists in medical technology will already be familiar with these state-of-the-art drive systems, they are not discussed further here.

FIG. 2 shows an axial section of the gearbox 12, which is housed in the handle sleeve 11 of the contra-angle, together with a rotation locking device 23. Front and rear drive shaft sections, 21 and 22 respectively, are driven by the compressed-air motor 13 via a planetary gear 24. Other suitable types of gearing can also be used instead of the planetary gear. Two bearings 30 and 31, preferably ball bearing assemblies, are used to house the drive shaft sections 21 and 22. When the motor is operated, the rotational movement of drive shaft sections 21 and 22 is transferred to a central drive 26 via a cog 25. The rotation locking device 23 is located in the connection area of the front and rear drive shaft sections 21 and 22. The gearbox 12 is surrounded by a bearing sleeve, or component 27 which is fixed, or secured, against rotation relative to body 11. The bearing sleeve 27 also acts, as is described more precisely in the following, as a buttress to the rotation locking device 23 when the user removes the tool from the coupling.

Figure 4:
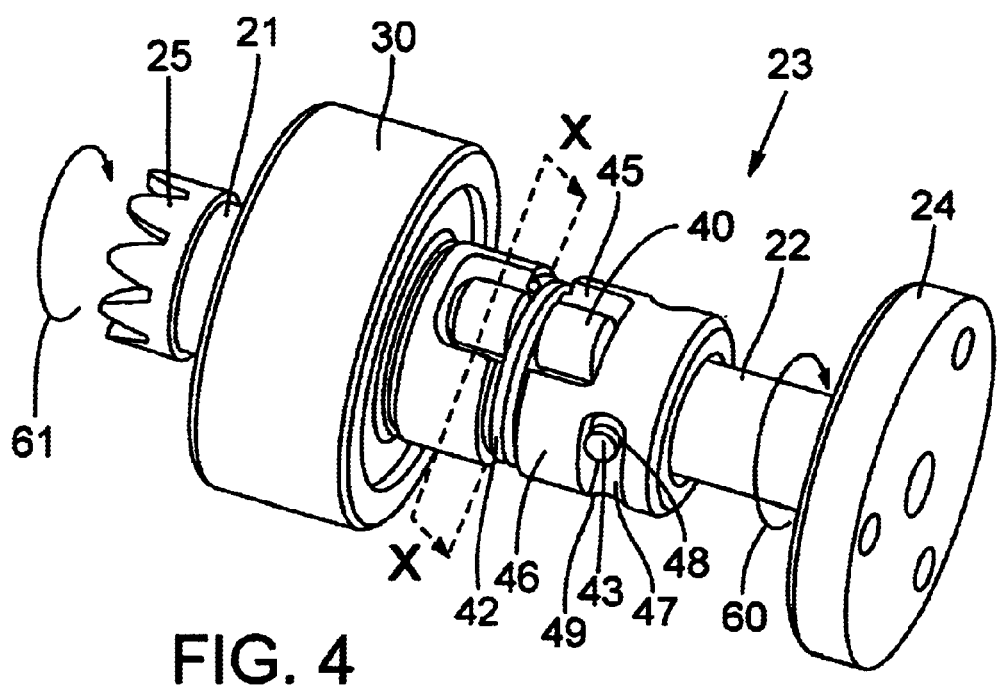
FIG. 4 shows a rotation locking device.

The rotation locking device is shown in more detail in FIGS. 3 and 4. A locking pin 40 sits on an indented displacement surface 44 of rear drive shaft section 22. In a preferred embodiment, the displacement surface 44 extends over approximately one quarter of the circumference of drive shaft section 22, but it may amount to any dimension which acts in accordance with the invention's functional principle.

In an example of the especially preferred embodiment, the shape of the displacement surface 44 is flat (see FIGS. 5A and 5B), but may also take the form of other profiles, e.g. curved or any shape which acts in accordance with the invention's functional principle. Some preferred profiles are shown in FIGS. 6A–6C: FIG. 6A shows the flat design which is very simple to manufacture from a production point of view. FIG. 6B shows a convex design and FIG. 6C a stepped profile, which make for smoother operation on account of the flowing transition from the displacement surface 44 to the part of the rear drive shaft section 22 which has not been indented or flattened.

The locking pin 40 is positioned on the displacement surface 44 by means of a recess 41 and a spring 42, which engages into the recess. Another pin 43 protrudes radially from the rear drive shaft section 22.

The rear drive shaft section 22 is connected to the compressed air motor 13 via the planetary gear 24, which is only partially shown in the diagram. A locking bush 46 connects the rear drive shaft section 22 to the front section 21. In doing so, pin 43 engages into a guide groove 47 located on the locking bush 46, while the locking pin 40 is positioned in a cut-out 45. Locking bush 46 can be manufactured on its own as a component and then subsequently connected to the front drive shaft section 21, e.g. by means of a pressing process or any other suitable method. In a preferred design example, the locking bush 46 is manufactured together with the front drive shaft section 21 as one component. During operation the rotational movement of the motor 13 is transferred to the central drive 26 via the cog 25.

Figure 5A:
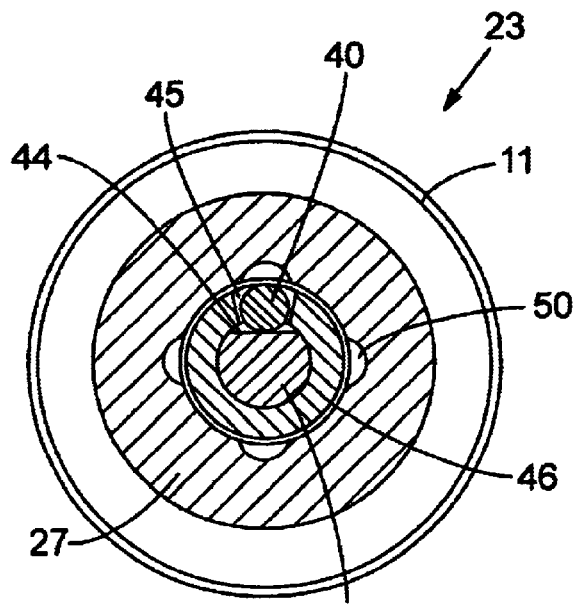
FIG. 5A shows a cross-section of the rotation locking device in its idle position.
Figure 6A:
FIGS. 6A–6C show the preferred profiles of the displacement surface for the rotation locking device.
Figure 6B:
Figure 5B:
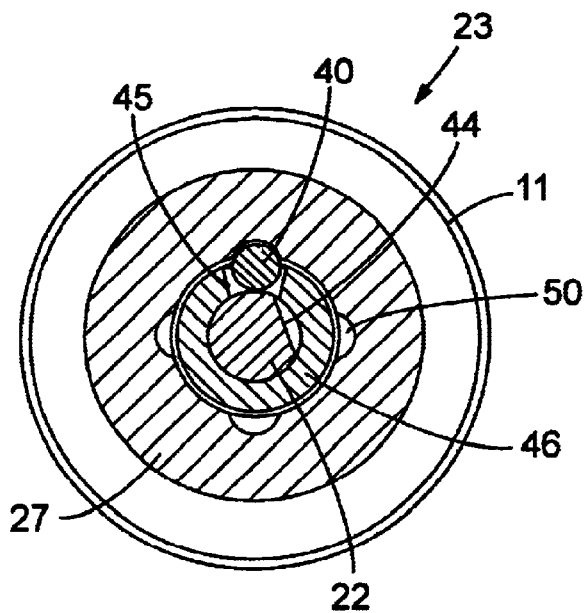
FIG. 5B shows a cross-section of the rotation locking device in its locked position (undesired rotation is blocked).
Figure 6C:
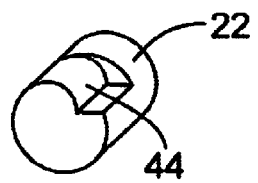

The way in which the rotation locking device 23 functions is shown in FIGS. 5A and 5B and is described below. The two cross-sections represent the rotation locking device 23 across the cross-sectional area marked with an X in FIG. 4. When the contra-angle 1 is operated, the rear drive shaft section 22 rotates in the direction represented by the arrow 60 in FIG. 4 (whereby the selected direction is arbitrary and the functional principle of the rotation locking device 23 is not dependent on the direction of drive). Rotation causes pin 43 to be moved in the guide groove 47 until it comes into contact with the upper end 48 of the guide groove and subsequently, via the locking bush 46, rotates the front drive shaft section 21 in the direction of the arrow 61. Meanwhile, the locking pin 40 assumes its idle position, i.e. it rests on the displacement surface 44 (see FIG. 3) and is thus in its lower, or non-locking position in the cut-out 45 of locking bush 46. This position is shown in FIG. 5A.

Should a tool change take place, then the user must turn the tool in the same direction as the drive shafts are rotated by the motor. This means that the front drive shaft section 21 and the locking bush 46 are rotated in the direction indicated by the arrow 61 until the lower end 49 of the guide groove 47 is pressed against the pin 43. The locking pin 40, rotating together with the locking bush 46, is moved away from the displacement surface 44 onto a part of the rear shaft section 22 which is not indented or flattened and is simultaneously forced out of the cut-out 45 radially (in relation to the axis of the drive shaft section), and then pressed against a component which is fixed to the body of the contra-angle; in a preferred embodiment this component is the bearing sleeve 27 of the gearbox 12. This situation is shown in FIG. 5B. In a preferred embodiment, an indentation 50, in which the pin can engage, is provided in the area in which the locking pin 40 presses against the bearing sleeve 27 in the housing of the gearbox 12. In the position shown in FIG. 5B, the locking pin 40 now prevents any further rotation of the front drive shaft section 21 and the user can remove the tool from the tool coupling without any problem. Once the user has unscrewed the tool and is thus no longer exerting any force on the front drive shaft section 21, the locking pin 40 is once again turned onto the displacement surface 44 by the force of the spring 42.

The invention is not restricted to the field of application shown and to the embodiment described here, but encompasses all design possibilities which do not change the main, analogous functional principle of the invention. In particular, the rotation locking device can be implemented between all shafts or shaft sections located between the motor and tool. The profile and number of the displacement surfaces 44, as well as the number of pins 43 and guide grooves, are not restricted to the examples quoted in the description. The geometric formation of the locking pin 40 can include any shape (preferred profiles are cylindrical, oval or conical) which supports the radial displacement of the locking pin 40. Any component fixed to the body of the appliance (e.g. handpiece or contra-angle 1) can act as a buttress for the locking pin 40, and the area in which the locking pin 40 is pressed against the component which is fixed to the body of the appliance can have corresponding indentations or surface structures.

What is claimed is:

1. A rotation locking device in an appliance having a body, the rotation locking device being located in the area of two separate, independent first and second shafts in the appliance for preventing undesired rotation of a shaft and comprising:
   an indented displacement surface on said first shaft; and
   a locking pin which rests on said displacement surface when in a non-locking position, and is displaced radially of the first shaft by undesired rotation of the second shaft, and is pressed against a non-rotating part of the appliance.

2. A rotation locking device according to claim 1, further comprising a locking bush extending about at least a portion of a shaft, said bush having a cut-out therein, and said locking pin is located in said cut-out.

3. A rotation locking device according to claim 2, wherein said locking bush is secured to said second shaft.

4. A rotation locking device according to claim 3, wherein said locking bush has a guide groove formed therein and a pin is connected to said first shaft, which pin moves in said guide groove.

5. A rotation locking device according to claim 1 wherein said non-rotating part has an indentation formed therein to receive a portion of said locking pin when said locking pin is displaced radially of the said first shaft.

6. A rotation locking device according to claim 1, wherein said appliance comprises a handpiece used in medical procedures.

7. A rotation locking device according to claim 1, wherein said appliance comprises a contra-angle used in dental treatment.

8. A rotation locking device according to claim 1 wherein the rotation locking device forms part of a gearbox in the appliance.

* * * * *